(12) United States Patent
Mirkin et al.

(10) Patent No.: US 7,569,340 B2
(45) Date of Patent: Aug. 4, 2009

(54) NANOARRAYS OF SINGLE VIRUS PARTICLES, METHODS AND INSTRUMENTATION FOR THE FABRICATION AND USE THEREOF

(75) Inventors: Chad A. Mirkin, Wilmette, IL (US); Rafael A. Vega, Evanston, IL (US); Daniel Maspoch, Evanston, IL (US); Khalid Salaita, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 11/506,200

(22) Filed: Aug. 18, 2006

(65) Prior Publication Data
US 2007/0129321 A1 Jun. 7, 2007

Related U.S. Application Data

(60) Provisional application No. 60/712,432, filed on Aug. 31, 2005.

(51) Int. Cl.
*C12Q 1/70* (2006.01)
*C12P 1/00* (2006.01)
*C12N 7/00* (2006.01)
*C12N 11/00* (2006.01)

(52) U.S. Cl. .......................... 435/5; 435/41; 435/235.1; 977/802

(58) Field of Classification Search ........................ None
See application file for complete search history.

(56) References Cited

U.S. PATENT DOCUMENTS 6,635,311 B1 10/2003 Mirkin et al.
6,827,979 B2 12/2004 Mirkin et al.
6,887,443 B2 5/2005 Liu et al.
2003/0068446 A1* 4/2003 Mirkin et al. ............ 427/430.1

FOREIGN PATENT DOCUMENTS

WO WO 2006/138272 A1 12/2006

OTHER PUBLICATIONS

Chueng, et al. Fabrication of Assembled Virus Nanostructures on Templates of Chemoselective Linkers Fromed by Scanning Probe Nanolithography. J Am Chem Soc. 2003; 125:6848-6849.*
U.S. Appl. No. 60/689,828, filed Jun. 13, 2005, Mirkin et al.
Advanced Inorganic Chemistry, $4^{TH}$ Ed., Coon and Wilkinson (1980).
Basu, G., et al., "Metal binding to cowpea chlorotic mottle virus using terbium(III fluorescence" *J. Biol. Inorg. Chem.*, vol. 8, 721-725 (2003).
Bohinski, R. C., Modern Concepts in BioChemistry, $4^{th}$ Ed. (1983).
Cann, A.J., *Principles of Modern Virology*, Academic Press (1993).

(Continued)

*Primary Examiner*—Mary E Mosher
*Assistant Examiner*—Stuart W Snyder
(74) *Attorney, Agent, or Firm*—Foley & Lardner LLP

(57) ABSTRACT

A nanoarray template utilizing coordination chemistry or metal ion binding to control the site-isolation and orientation of virus particles is provided. The nanoarray template is generated by lithography including Dip Pen Nanolithography. The surface chemistry that is inherent in many viruses, metal-ion based or inorganic coordination chemistry is used to immobilize individual virus particles without the need for their genetic modification. Single particle control enables a wide variety of studies involving viruses that are not possible with microarrays, including single particle, single cell infectivity studies, exploration of such structures as templates in materials synthesis and molecular electronics, and studies aimed at understanding how surface presentation influences their bioactivity. This is an example of such control at the single-particle level, and therefore, commercial use of nanoarrays in biological systems.

22 Claims, 7 Drawing Sheets

OTHER PUBLICATIONS

Cheung, C. L., et al., "Fabrication of Assembled Virus Nanostructures on Templates of Chemoselective Linkers Formed by Scanning Probe Nanolithography" *J. Am. Chem. Soc.*, vol. 125, 6848-6849 (2003).

Chiu, W., Burnett, R.M., and Garcea, R.L. (Eds), *StructuralBiology of Viruses*, Oxford University Press (1997).

Demers, L. M., et al., "Direct Patterning of Modified Oligonucleotides on Metals and Insulators by Dip-Pen Nanolithography", *Science*, vol. 296, 1836-1838 (2002).

Direct-Write Technologies for Rapid Prototyping Applications (Ed. Alberto Pique and D.B. Chrisey), Academic (2002).

Dujardin, E., et al., "Organization of Metallic Nanoparticles Using Tobacco Mosaic Virus Templates", Nano Lett., vol. 3, 413-417 (2003).

Fraser, R. D. B., Infra-Red Dichroism of Tobacco Mosaic Virus Nucleoprotein, *Nature*, vol. 29, 491 (1952).

Frey, B. L., et al., "Covalent Attachment and Derivatization of Poly(L-lysine) Monolayers on Gold Surfaces As Characterized by Polarization-Modulation FT-IR Spectroscopy", *Anal. Chem.*, vol. 68, 3187-3193 (1996).

G. MacBeath, Printing Proteins as Microarrays for High-Throughput Function Determination, *Science*, vol. 289, pp. 1760-1763 (2000).

Ginger, D. S., "The Evolution of Dip-Pen Nanolithography", *Angew Chem. Int. Ed.*, 43, 30-45 (2004).

Guthold, M., et al., "Investigation and modification of molecular structures with the nanoManipulator", *J. Mol. Graphics Mod.*, vol. 17, 187-197 (1999).

Heller, R. A., "Discovery and analysis of inflammatory disease-related genes using cDNA microarrays", *Proc. Natl. Acad. Sci. USA*, vol. 94, pp. 2150-2155 (1997).

Hyun, J., et al., "Capture and Release of Proteins on the Nanoscale by Stimuli-Responsive Elastin-Like Polypeptide 'Switches'", *J. Am. Chem. Soc.*, vol. 126, 7330-7335 (2004).

King, L., et al., "Derivatisation of Carboxyl Groups of Tobacco Mosaic Virus with Cystamine", *Biochim. Biophys. Acta*, vol. 322, 279-293 (1973).

Knez, M., et al., "Binding the Tobacco Mosaic Virus to Inorganic Surfaces", *Langmuir*, vol. 20, 441-447 (2004).

Knez, M., et al., "Biotemplate Synthesis of 3-nm Nickel and Cobalt Nanowires", *Nano Lett.*, vol. 3, 1079-1082 (2003).

Lee, K.-B., et al., "Protein Nanoarrays Generated By Dip-Pen Nanolithography", *Science*, vol. 295, 1702-1705 (2002).

Lindroos, K., "Multiplex SNP genotyping in pooled DNA samples by a four-colour microarray system", *Nucleic Acid Res.*, vol. 30, pp. e70-e78 (2002).

Maeda, H., "An Atomic Force Microscopy Study for the Assembly Structures of Tobacco Mosaic Virus and Their Size Evaluation", *Langmuir*, vol. 13, 4150-4161 (1997).

Miller, U. R., *Microarray Technology and Its Applications*, Springer, New York (2005).

Schena, M., "Quantitative Monitoring of Gene Expression Patterns with a Complementary DNA Microarray", *Science*, vol. 270, pp. 467-470 (1995).

Shenton, W., et al., "Inorganic-Organic Nanotube Composites from Template Mineralization of Tobacco Mosaic Virus", *Adv. Mater.*, vol. 11, 253-256 (1999).

Smith, J. C., "Nanopatterning the Chemospecific Immobilization of Cowpea Mosaic Virus Capsid", *Nano Lett.*, vol. 3, 883-886 (2003).

Vega, R. A., "Nanoarrays of Single Virus Particles", Chem. Int. Ed., vol. 44, No. 2-4, pp. 6013-6015 (2005).

Wilson, T. M. A., "Modification of the Coat Protein Charge and Its Effect on the Stability of the $U_1$ Strain of Tobacco Mosaic Virus as Alkaline pH", *Virology*, vol. 140, 21-27 (1985).

Rozhok, S. et al., "Methods for fabricating microarrays of motile bacteria," Small (Weinheim an der Bergstrasse, Germany), vol. 1, No. 4, pp. 445-451, XP002470255, ISSN: 1613-6829 (2005).

Salaita, K., et al., "Sub-100 nm, centimeter-scale, paraleel dip-pen nanolithography," Small (Weinheim an der Bergstrasse, Germany), vol. 1, No. 10, pp. 940-945, XP002470257, ISSN: 1613-6829 (2005).

Vega, R. A., et al., "Functional antibody arrays through metal ion-affinity templates," Chemobiochem, vol. 7, No. 11, pp. 1653-1657, 1632, XP002470256, ISSN: 1439-4227 (2006).

Search Report, PCT/US2006/032316, dated Mar. 6, 2008 (2 pages).

\* cited by examiner

NANOARRAYS OF SINGLE VIRUS PARTICLES, METHODS AND INSTRUMENTATION FOR THE FABRICATION AND USE THEREOF

RELATED APPLICATIONS

This application claims priority benefit to provisional application Ser. No. 60/712,432 filed Aug. 31, 2005 to Mirkin, et al., which is hereby incorporated by reference in its entirety.

GOVERNMENT RIGHTS

This invention was made with government support under following grants: Air Force Office of Science Research (AFOSR) grant MURI F49620-00-1-0283; NIH grant 1DP1OD000285-01; NSF/NSEC grant EEC-0118025; DARPA/AFOSR grant FA9550-05-1-0348; and ARO-MURI 28065-3-A1//W91NF-04-1-071. The government has rights in this invention.

BACKGROUND

Microarray technology has led to significant advances in many areas of medical and biological research,[1] opening up avenues for the combinatorial screening and identification of single nucleotide polymorphisms (SNPs),[2] high sensitivity expression profiling of proteins,[3,4] and high throughput analysis of protein function.[5] However, current microarraying technologies, such as spotting with pin arrays, inkjet printing or methods derived from photolithography, are limited in their practical resolution—from hundreds to tens of microns, depending on the technique. The density of the fabricated arrays and therefore the number of distinct deposited biological entities (which include but are not limited to proteins, nucleic acids, carbohydrates, lipids, and especially complex or assemblies thereof, such as viruses or cell components) are therefore limited. There is therefore a need for a method capable of few-microns and sub-micron-scale arraying of said biological entities.

In addition, the dimensions of each site in currently fabricated microarrays are typically much larger than the size of individual biological molecules or assemblies being deposited. Therefore, large numbers of said entities are present in each site and only the statistical, collective behavior of these ensembles can be studied. Isolated biological particles have been deposited at random on solid substrates by e.g. contacting a very dilute solution of said biological particles with a solid substrate with carefully selected surface chemistry during a carefully selected amount of time, optionally followed by rinsing steps. This method offers little if any control over the density and placement of said particles. There is therefore a need for a miniaturization method—down to the nanometer length scale—with the potential to "site-isolate" nano- and microscale biological entities at the single-particle level with precise positioning. With such method, new opportunities will be available to the biochemical and biomedical research communities to begin to study such entities individually rather than collectively. Site-isolation is of commercial interest, e.g. in pharmaceutical R&D during drug discovery—especially to rapidly elucidate the fundamental mechanism of interaction between a drug candidate and its target—without need for difficult and time-consuming techniques like crystallization and X-ray analysis. Other commercially relevant single particle biology experiments include, for example, studying (a) the effect of the relative orientation between biological entities on their interactions; (b) the cooperative behavior of a selected number of pathogens infecting simultaneously e.g. a cell; (c) the binding of a single antibody with an antigen or conversely the cooperative behavior of multiple antibodies towards an antigen; (d) variations in the interaction of a target drug with individual forms of a polymorphic protein or that of various members of the same protein family; and (e) the effect of genetic variations among viruses in an array on their interaction with another biological item.

Prior to this invention, advances have been made in immobilizing virus particles on templates created by DPN and micro-contact printing.[11,12] However, a need exists to provide the ability to chemically control the position of the immobilized virus structures at the single-particle level. This is in part because of limited resolution (vide supra), the size of the particles interrogated, and especially the chemistry used to immobilize them. Indeed, prior efforts have focused on the genetic modification of a virus particle to present unnatural surface binding functionality to the patterned interface.[11, 12] For reasons of cost and scalability, it is preferable to avoid manipulation of said viruses. There is therefore a need for a method to chemically control the position of the immobilized virus structures at the single-particle level without need for chemical or genetic modification of said viruses.

No admission is made that any of the references cited in this Background section or thereafter are prior art.

SUMMARY OF THE INVENTION

The following is a non-limiting summary of the invention. Further embodiments are found in the detailed description and claims.

The invention generally relates to arrays of biological entities and in particular arrays of site-isolated biological entities. It further relates to (a) the use of direct-write nanolithographic printing for the fabrication thereof; and (b) methods of use of these arrays.

The present invention in some embodiments provides arrays of biological particles, in which at least one of the lateral dimensions of the sites is in the few-microns or sub-micron range (including nanoarrays). The invention also discloses organized, engineered arrays of site-isolated biological particles and especially arrays of site-isolated virus particles.

For example, one embodiment provides an array comprising: a substrate surface, wherein the substrate surface comprises virus binding sites and also sites which do not bind virus, wherein the virus binding sites on the substrate surface each have a shape and a size; and one virus particle disposed on each of the binding sites. The shape and size of the virus binding site provides that only one virus particle is disposed on each binding site. The substrate surface can be substantially flat.

Another embodiment provides an array comprising: a plurality of virus binding sites on a substantially flat substrate surface, wherein the sites are surrounded by passivated substrate surface passivated against virus binding, wherein the virus binding sites comprise ionic groups for binding virus and have a shape and size so that only one virus particle binds to each site, and wherein the average size of the virus binding sites provides a surface area of about 30,000 square nm to about 100,000 square nm for each site.

Another embodiment provides an array comprising: a plurality of virus binding sites on a substantially flat substrate surface, wherein the sites are surrounded by passivated substrate surface passivated against virus binding, wherein the virus binding sites have a shape and size so that only one virus particle binds to each site, wherein the average size of the virus binding sites provides a surface area of about 30,000 square nm to about 100,000 square nm for each site, one virus bound to each site, wherein the virus in an unbound shape presents a cross-sectional surface area which is less than about 100,000 square nm.

Another embodiment provides a method of making an array comprising the combination of steps: providing a substrate surface, modifying the substrate surface to provide virus binding sites and also sites which do not bind virus, binding virus to the virus binding sites so that substantially only one virus particle binds to each site.

In a preferred embodiment, the shape and the size of the virus binding site in the array provides that only one virus particle is disposed on each binding site. The sites which do not bind virus may be passivated against virus binding and may be substantially free of virus. The virus binding sites may comprise ionic binding sites. The average size of the virus binding sites provides a surface area of less than about 100,000 square nm for each site, or less than about 50,000 square nm for each site, or about 30,000 square nm to about 100,000 square nm for each site. The shape of the virus binding sites may be substantially a circle, a linear shape, a curvilinear shape, a square, or a rectangle. The shape of rectangular virus binding sites may comprise a rectangle having a length of about 300 nm to about 600 nm, and a width of about 100 nm to about 200 nm. The virus itself may have a substantially spherical shape or it may have an anisotropic shape and especially a tubular shape. The virus particle may comprise at least one additional moiety bound to the virus, such as a protein. The virus binding sites and the sites which do not bind virus may also comprise a monolayer. The shape and size of each of the virus binding sites may be substantially the same, or the shape or size may be different.

In an especially preferred embodiment, the invention provides an array comprising a plurality of virus binding sites on a substantially flat substrate surface, wherein the sites are surrounded by substrate surface passivated against virus binding, wherein the virus binding sites comprise ionic groups for binding virus and have a shape and size so that only one virus particle binds to each site, and wherein the average size of the virus binding sites provides a surface area of about 30,000 square nm to about 100,000 square nm for each site.

The invention further provides an array comprising (a) a plurality of virus binding sites on a substantially flat substrate surface, wherein the sites are surrounded by substrate surface passivated against virus binding, wherein the virus binding sites have a shape and size so that only one virus particle binds to each site, wherein the average size of the virus binding sites provides a surface area of about 30,000 square nm to about 100,000 square nm for each site; and (b) one virus bound to each site, wherein the virus in an unbound shape presents a cross-sectional surface area which is less than about 100,000 square nm.

The invention further discloses methods, kits and instruments for the fabrication and use of said arrays.

In another embodiment, the invention provides a method of making an array comprising the steps: providing a substrate surface, modifying the substrate surface to provide virus binding sites and also sites which do not bind virus, binding virus to the virus binding sites so that substantially only one virus particle binds to each site.

Another embodiment provides an array consisting essentially of: a substrate surface, wherein the substrate surface comprises virus binding sites and also sites which do not bind virus, wherein the virus binding sites on the substrate surface each have a shape and a size; and one virus particle disposed on each of the binding sites, wherein the shape and the size of the virus binding site provides that only one virus particle is disposed on each binding site. A basic and novel feature is the use when needed of excluding or substantially excluding components which compromise the advantages of the invention.

In conclusion, a versatile coordination, metal-ion based chemistry based approach is described for immobilizing TMV virus particles on surfaces and shown that through the use of DPN and small features, it is possible to isolate and control the orientation of these virus particles. Many virus particles have $Zn^{2+}$ and other metal-binding groups in their protein coats.[18] Therefore, this approach can be generalized for manipulating many classes of virus structures at the single-particle level. Such capabilities will expand the scope of application for virus structures in fields ranging from biology to molecular electronics,[19] where such control opens new opportunities for research that cannot be addressed with microarrays or bulk systems.

DETAILED DESCRIPTIONS OF THE PREFERRED EMBODIMENTS

Introduction

Figure 1:
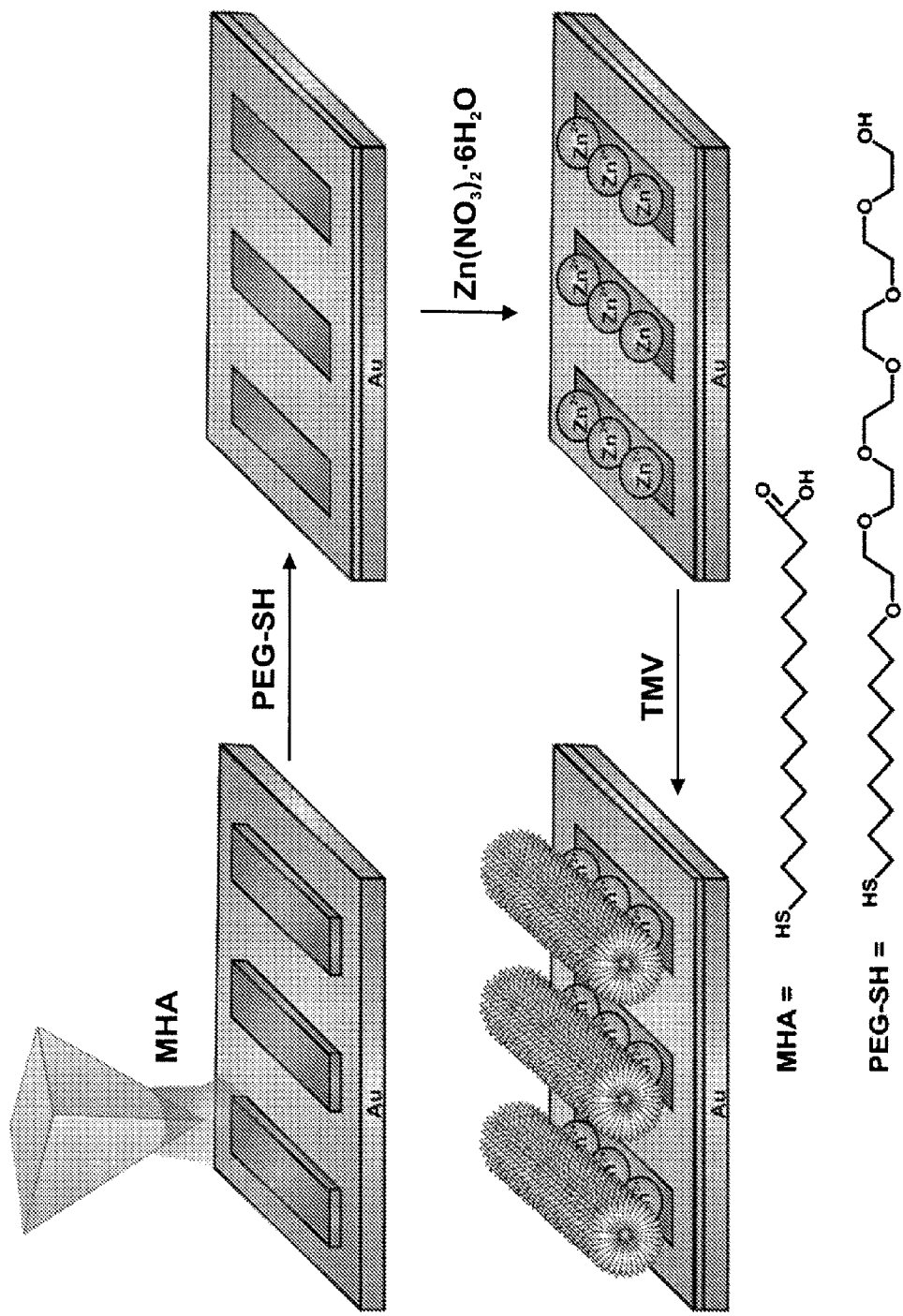
FIG. 1. Schematic diagram describing the selective immobilization of single virus particles on DPN-generated MHA nanotemplates treated with a solution of $Zn(NO_3)_2.6H_2O$. The diagram is not to scale.

References will be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

All references in this specification are incorporated by reference in their entirety and can be relied upon in general in practicing the invention.

Priority provisional application Ser. No. 60/712,432 filed Aug. 31, 2005 to Mirkin et al. is hereby incorporated by reference in its entirety.

The following reference is incorporated hereby by reference in its entirety: "Nanoarrays of Single Virus Particles", Rafael A. Vega, Daniel Maspoch, Khalid Salaita, and Chad A. Mirkin, Angew. Chem. Int. Ed. 2005, 44, 2-4, 6013-6015.

U.S. provisional Ser. No. 60/689,828 filed Jun. 13, 2005 to Mirkin et al., and PCT Patent Application Serial No. PCT/2006/022929 "Metal-Ion Based Immobilization" filed Jun. 13, 2006 to Mirkin, et al. also describes metal ion binding technology and is hereby incorporated by reference in its entirety including summary, drawings, detailed description, claims, abstract, and sections on biological species, proteins, antibodies, metal binding proteins, cells/viruses, metal ions, surface functionalization, compounds, patterning, surface passivation, methods, passivation agents, surfaces, substrates, products, and working examples and schemes.

Arrays

The present invention discloses arrays of biological particles (such as cells and cellular components, bacterial elements, spores, viruses, and other assemblies and complex of proteins, including antibodies, nucleic acids, lipids and carbohydrates), in which at least one of the lateral dimensions of the sites is in the few-microns or sub-micron range (including nanoarrays). In a preferred embodiment, the invention discloses organized, engineered arrays of site-isolated biological particles and especially arrays of site-isolated virus particles. The arrays may comprise 100 or more, or preferably 1000 or more or preferably 10,000 or more biological entities or preferably 100,000 or more biological entities. Said biological entities may be identical or not.

Virus

Virus arrays are a preferred embodiment and working examples are shown thereafter that demonstrate TMV arrays. However, the invention is not limited to this or any other plant virus. Animal and human virus may also be utilized, including HIV, respiratory track and flu viruses.

Viruses can be used which are generally known for those of ordinary skill in the art, see e.g. Cann, A. J., *Principles of Modern Virology*, Academic Press, 1993; Chiu, W., Burnett, R. M., and Garcea, R. L. (Eds), *StructuralBiology of Viruses*, Oxford University Press, 1997. See also R. C. Bohinski, Modern Concepts in BioChemistry, $4^{th}$ Ed., 1983.

For example, a virus used herein can be a particle that can infect a cell of a biological organism. An individual virus, or a virus particle, also can be called a virion, can comprise one or more nucleic acid molecules, so called viral genome, surrounded by a protective protein coat known as a capsid. Unlike cellular organisms, in which the nucleic acid molecules are generally made up of DNA, the viral nucleic acid molecule may comprise either DNA or RNA. In some cases, viral nuclear acid molecules comprise both DNA and RNA. Viral DNA is usually double-stranded, either a circular or a linear arrangement, while viral RNA is usually single-stranded. However, examples of single stranded viral DNA and double-stranded viral RNA are also known. Viral RNA may be either segmented (with different genes on different RNA molecules) or nonsegmented (with all genes on a single piece of RNA). The size of the viral genome can vary significantly in size. Both DNA and RNA viruses can be used herein.

In viruses used herein, the viral capsid can comprise repeating units of one or a few different proteins coded by the viral genome. These units are called protomers or capsomers. These proteins that make up the virus particle can be called structural proteins. A number of structural proteins in the viral particle can vary from one (e.g, Satellite tobacco Necrosis Virus) to 377 (*Paramecium bursaria Chlorella* virus).

Viruses used herein can have a variety of shapes. For example, the viral capsid can be helical (spiral-shaped) or icosahedral. One example of a virus with a helical viral capsid is tomato mosaic virus, while examples of viruses isosahedral viral capsids include Tomato Bushy Stunt Virus and Simian Virus 40. Some more complex viruses can have a capsid that is neither purely helical, nor purely isosahedral. Some more complex viruses may possess extra structures such as protein tails or a complex outer wall. For example, some bacteriophages, i.e. viruses that can infect bacterial cells, may have a capsid comprising isosohedral head bound to a helical tail, which may also have a hexagonal base plate with many protruding protein fibres.

Viral capsid and the viral genome contained therein can be together referred to as nucleocapsid. Some virus particles comprise nucleocapsids, while others contain additional structures. For example, some viruses can be enclosed in a lipid envelope acquired when the virus buds through host-cell membranes. One or more glycoproteins that bind virus particles to susceptible host cells can be inserted into this envelope. The glycoproteins can be coded by both the viral genome and the host cell genome, while the envelope's lipids and any carbohydrates present are entirely host cell's genome coded.

Viruses can vary in size, as used herein. For example, a diameter of the viral capsid can be from about 10 nm to about 400 nm, usually about from about 10 nm to about 300 nm. Some virusal capsides can have a significant length to diameter ratio. For example, capsids of some filoviruses can have a length up to 1400 nm and a diameter of only 80 nm.

Viruses can be classified according to their type of genetic material, their strategy of replication, and their structure. According to their genome and strategy of replication, viruses can be classified as follows:

A) DNA Viruses:
  Group I: viruses comprising double-stranded DNA. Examples include such virus families as Herpesviridae (herpes viruses) and Poxviridae (chickenpox and smallpox), many tailed bacteriophages, and a virus with the largest known viral genome, mimivirus.
  Group II: viruses comprising single-stranded DNA. Examples include such virus families as Parvoviridae and bacteriophage M13.
B) RNA Viruses:
  Group III: viruses comprising double-stranded RNA genomes. These genomes are segmented.
  Group IV: viruses comprising positive-sense single-stranded RNA genomes. Examples include SARS virus, hepatitis C virus, yellow fever virus and rubella virus.
  Group V: viruses comprising negative-sense single-stranded RNA genomes. Examples include filoviruses such as Ebola and Marburg viruses along with measles, mumps and rabies.
C) Reverse Transcribing Viruses:
  Group VI: viruses that comprise single-stranded RNA genomes and replicate using reverse transcriptase. Examples include retroviruses such as HIV virus.
  Group VII: viruses that comprise double-stranded DNA genomes and replicate using reverse transcriptase. Example includes hepatitis B virus.

The virus can have for example an anisotropic shape. For example, the virus can have a tubular shape.

The virus can comprise an additional moiety bound to the virus.

Genetically engineered viruses and synthetically modified viruses can be used. See for example Genetically Engineered Viruses, Ed. C J A Ring, E. D. Blair, 2001.

In many cases, the virus can be used as is or as a wild type without modification.

In addition to viruses, other pathogens, including cellular parasites like malaria, are possible. Cell organelles (including but not limited to ribosomes, cellular nuclei, and other vesicles and cellular apparatuses) are also possible.

Substrate Surface

The substrate surface is not particularly limited but can be for example substantially flat. Substrates such as glass or metals can be used. Microfabrication methods can be used to prepare substrates and build up layers and appropriate surfaces. The virus binding sites and the sites which do not bind virus can comprise for example a monolayer. A thin layer of organic compound can form a monolayer over an inorganic substrate.

Binding Sites

The binding sites can comprises regions with a plurality of molecular binding sites. The virus binding sites can comprise ionic binding sites. These can be for example multivalent metallic ionic binding sites including di- or tri- or tetravalent binding sites. Metals, metal ions, and metal ion binding is generally described in for example, Advanced Inorganic Chemistry, 4$^{th}$ Ed., Cotton and Wilkinson, 1980.

An exemplary approach used herein relies on the ability of ions, such as metal ions and divalent metal cations (e.g. $Zn^{2+}$ which is preferred; other ions are possible) to bridge a surface patterned with features that carry an opposite charge, for example the terminal groups of a self-assembled monolayer (e.g. 16-mercaptohexadecanoic acid, MHA) or the external surface of a charged biological entity, such as a carboxylate-rich virus envelope. Other molecules that bind to said substrate and present a suitable functional group (e.g. omega-functionalized alkanethiols or organosilanes) are possible.

Metal ion binding can be carried out with metals including for example Zn(II), Cu(II), Ni(II), and Co(II). The metal ion is not particularly limited but can be based on for example ionic forms of ruthenium, cobalt, rhodium, rubidium, vanadium, cesium, magnesium, calcium, chromium, molybdenum, aluminum, iridium, nickel, palladium, platinum, iron, copper, titanium, tungsten, silver, gold, zinc, zirconium, cadmium, indium, and tin. Divalent metal cations include $Cd^{2+}$, $Zn^{2+}$, $Pb^{2+}$, $Cu^{2+}$, and $Ni^{2+}$.

Protein and peptide nanoarrays and binding sites are also described in for example US Patent Publication 2003/0068446 to Mirkin et al., which is hereby incorporated by reference.

In designing metal-based binding sites, principles of IMAC (Immobilized Metal Affinity Chromatography) can be used. See for example U.S. Pat. Nos. 5,932,102 and 6,942,802.

In some embodiments, binding sites are adapted so that the virus maintains its shape despite binding and does not substantially deform.

Sites which do not Bind Virus

Additional parts of the surface can be passivated to prevent and substantially prevent binding of virus. As a result, the sites which do not bind virus can be substantially free of virus. Passivation is generally known as described in for example US Patent Publication 2003/0068446 to Mirkin et al. A monolayer can be coated onto the substrate to provide passivation such as for example an alkane thiol or a linear alkane thiol, or an alkane thiol comprising a terminal group, as well as alkane thiols including a poly- or oligo-alkyleneglycol thiol.

Size and Shape of Binding Sites for Single Site Binding

The substrate binding site and sites can be adapted so that only one virus particle is disposed on each binding site. In an array, an occasional binding site can have more than one virus particle so that for example at least 70%, or at least 80%, or at least 90% of the binding sites have one virus particle. The invention further provides a method to engineer at known locations micro- to nanometer-scale sites, which geometry and dimensions approach that of the targeted biological particles, so that only a selected number of particles may be deposited on each site. Preferably, only about one particle may adsorb on each site. Furthermore, many such sites may be produced in parallel very rapidly, and precise positioning, orientation and inter-particle spacing can be guaranteed.

For example, the longest lateral dimension of each site may be between 5 microns and 1 micron, or between 1 micron and 500 nm or between 500 nm and 300 nm or between 300 nm and 100 nm or inferior to 100 nm or smaller than 50 nm.

The site may be, for example, substantially a circle, a linear shape, a curvilinear shape, a square, or a rectangle. It can be for example rectangular, square or disk-like.

Rectangular sites may be between 600 nm×200 nm and 500 nm×180 nm, or between 500 nm×180 nm and 400 nm×150 nm or between 400 nm×150 nm and 350 nm×110 nm, in length and width. The shape can be for example a rectangle having a length of about 300 nm to about 600 nm, and a width of about 100 nm to about 200 nm.

Dot-shaped sites may be between 1000 nm and 500 nm diameter or preferably between 500 nm and 350 nm diameter, or preferably between 350 nm and 100 nm in diameter or preferably smaller than 100 nm in diameter.

The separation between sites may be between 15 microns and 5 micron, or between 5 microns and 1 micron or between 1 micron and 500 nm or between 500 nm and 100 nm or inferior to 100 nm or smaller than 50 nm.

The average size of the virus binding sites can provide for example a surface area of less than about 100,000 square nm, or less than about 50,000 square nm, or about 30,000 square nm to about 100,000 square nm, for each site.

Lithography

Methods of patterning, printing, drawing, writing, microlithography, and nanolithography are known in the art and include direct write lithography and direct-write nanolithography. See for example Direct-Write Technologies for Rapid Prototyping Applications,(Ed. Alberto Pique and D. B. Chrisey), Academic, 2002.

Examples of lithography and direct write lithography with respect to bioarrays include for example AFM-tip based lithography, DPN printing, microcontact printing, robotic spotting, and the like.

In one embodiment, the invention improves high resolution direct-write lithographic methods such as Dip Pen Nanolithography (DPN)[6] for miniaturizing biological entity structures to the nanometer length scale[7-9] (DPN™, Dip Pen Nanolithography™, NanoInk™, DPNWrite™, NScriptor™ are trademarks or registered trademarks of NanoInk, Inc., Chicago, Ill.). See also for example Ginger et al., Angew. Chem. Int. Ed. Engl., 2004, 43, 30-45 as well as U.S. Pat. No. 6,635,311 to Mirkin et al.; U.S. Pat. No. 6,827,979 to Mirkin et al, and U.S. Pat. No. 6,887,443 to Liu et al. for additional embodiments for tip based nanolithography including instrumentation, software, inks, and processes, which are hereby incorporated by reference in their entirety. Such massive miniaturization provides the advantages of larger, denser libraries for screening complex chemical and biological systems.

In a preferred embodiment, the ion-trapping sites may be fabricated using direct-write nanolithographic printing such as DPN printing.

If desired, ink mixtures comprising multiple inks or dual phase ink systems can be used as described in for example U.S. Ser. No. 11/480,557 filed Jul. 5, 2006 to Mirkin et al.

Method of Manufacture and Use

Additionally, the invention describes a novel technology that utilizes DPN printing in combination with metal ions or coordination chemistry to precisely immobilize and position biological particles in the context of large arrays. In a second embodiment, the method to precisely immobilize at least one biological particle on a substrate without unnatural genetic or chemical modification of said biological particle prior to immobilization comprises the steps of (a) patterning a substrate, forming an array of sites capable of trapping ions, for example metallic cations such as those of Zinc (e.g. $Zn^{2+}$) or $copper^{2+}$ or $nickel^{2+}$; (b) optionally passivating the areas of the substrate that were not patterned with at least one compound that prevents ion and biological entity adsorption; (c) selectively trapping said ions on top of said sites e.g., by immersion of said substrate in a solution of said ion; (d) selectively immobilizing said biological particle on said sites, e.g. by immersion of said substrate in a solution of said biological particle.

In another embodiment, the invention provides a method for immobilizing about a single biological particle per site of the nanometer-scale array, resulting in the production of site-isolated biological entities at known locations, wherein said isolation of biological entities is not the result of random adsorption from a very dilute solution.

In another embodiment, the invention provides a method for the fabrication of arrays of biological particles, wherein most of the biological particles assume a specific orientation or shape. Preferably, said orientation or shaping is provided by chemical means rather than physical means, e.g. by the interplay of the geometry and surface chemistry of said site and these of the external surface of said biological entity, rather than by the application of an external electrical, magnetic field or use of fluid flow.

Properties of Array

Preferably, the method allows the deposition of said biological particles in such manner that they remain biologically active. Biological activity may be verified, for example, by the binding of antibodies specific to said biological particles onto said particles or by the formation of Watson-Crick pairs with complementary nucleic acid strands present in solution. Properties can be examined by scanning probe methods.

Additional Embodiments

The invention further discloses methods, kits and instruments for the fabrication and use of said arrays:

The invention also provides a kit for the fabrication of arrays of site-isolated biological entities that comprises a substrate, at least one probe, a chemical composition, a passivating solution, an ionic solution, and a biological entity solution, wherein the chemical composition is adapted to coat the at least one probe and being deposited on the substrate to form at least one pattern, wherein the passivating solution can passivate unpatterned areas of the substrate, wherein immersing the patterned and passivated substrate in the ionic solution afford ions selectively bound to patterned regions, wherein the biological entities may adsorb to ion-treated patterned regions.

The invention also provides an instrument capable of the fabrication of arrays of site-isolated biological entities, the instrument comprising at least one probe and fluid dispensing means for delivering the solutions of the aforementioned kit in sequence. Multiprobe AFM based lithographic methods can be used. Activated probes can be used. The instrument may be for example a modified atomic force microscope capable of direct-write nanolithographic printing and the probe may be an AFM cantilever with or without a tip or an SPM probe.

The invention also provides an instrument and a method for the observation and characterization of the interaction of an isolated biological particle with at least one second biological entity of at least one type.

WORKING EXAMPLES

Non-limiting working examples are provided.

Working Example

Site-Isolated TMV Arrays

In this example, virus particles were site-isolated, positioned and oriented on $Zn^{2+}$-MHA nanotemplates generated by dip pen nanolithography. Viral immobilization was characterized using antibody-virus recognition as well as infrared spectroscopy.

The approach used in this working example relied on the ability of metal ions ($Zn^{2+}$) to bridge a surface patterned with features made of 16-mercaptohexadecanoic acid (MHA) and the TMV with its carboxylate-rich surface.

Tobacco Mosaic Virus (TMV) was chosen because of its anisotropic tubular structure (about 300 nm long, 18 nm diameter), size, stability, and well -characterized carboxylate-rich surface.[10] It serves as an excellent demonstrative system to evaluate how one can use DPN to control the positioning and orientation of nanoscale virus particles within an extended array.

Figure 2:
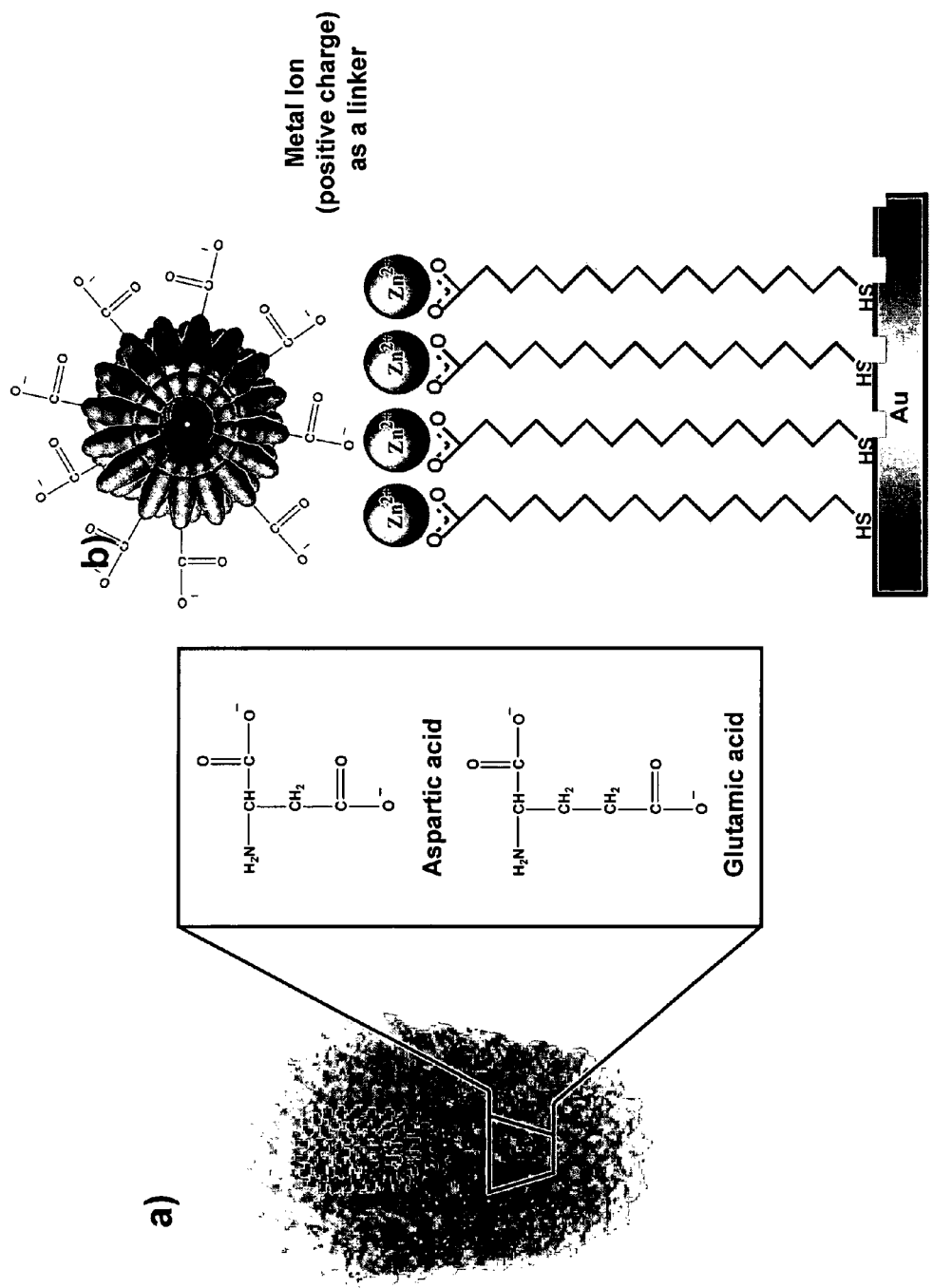
FIG. 2. Schematic diagram describing (a) the Tobacco Mosaic Virus (TMV) external surface, which presents a high number of carboxylic/carboxylate groups from glutamate and aspartate amino acids. TMV is deprotonated at pH 3.5; (b) the sandwich formed by the carboxylate groups of the mercaptohexadecanoic acid self-assembled monolayer pattern, on one hand, the Zinc cations and the carboxylate groups present on the TMV virus, on the other hand. Without wishing to be bound by theory, it is believed that the electrostatic bridge formed by the positively charged zinc ions and the negatively charged carboxylates is responsible for the immobilization of said TMV virus on said MHA pattern. The diagram is not to scale.

Virus nanoarrays were fabricated by initially generating chemical templates of MHA on a gold thin film using DPN (FIG. 1). The regions surrounding these features were passivated with a monolayer of 11-mercaptoundecyl-penta(ethyleneglycol) (PEG-SH) by immersing the substrate in an alkanethiol solution (5 mM in ethanol) for 30 minutes followed by copious rinsing with ethanol. The passivation layer minimizes nonspecific binding of the virus particles to the unpatterned areas. The carboxylic acid groups of MHA were coordinated to $Zn^{2+}$ ions by exposing the substrate to an ethanol solution of $Zn(NO_3)_2.6H_2O$ (5 mM) for one hour followed by rinsing with ethanol to remove any unbound metal ions from the surface (see also, FIG. 2). The metallated substrate was then exposed to a 0.15 M NaCl 10 mM phosphate buffer pH 7 (PBS) solution containing TMV (from American Type Culture Collections) (100 microg/mL) for 24 hours at room temperature in an air-tight humidity chamber. Excess virus particles were removed by washing the substrates with NANOpure water. The cleaned substrates were then dried under a stream of $N_2$. All virus arrays were characterized by tapping mode AFM (TMAFM), and the chemical identity of the surface-immobilized virus particles was confirmed by treatment with a highly specific antiserum (from American Type Culture Collections) against TMV, which upon binding, increases the height of each virus particle (vide infra).

Figure 3:
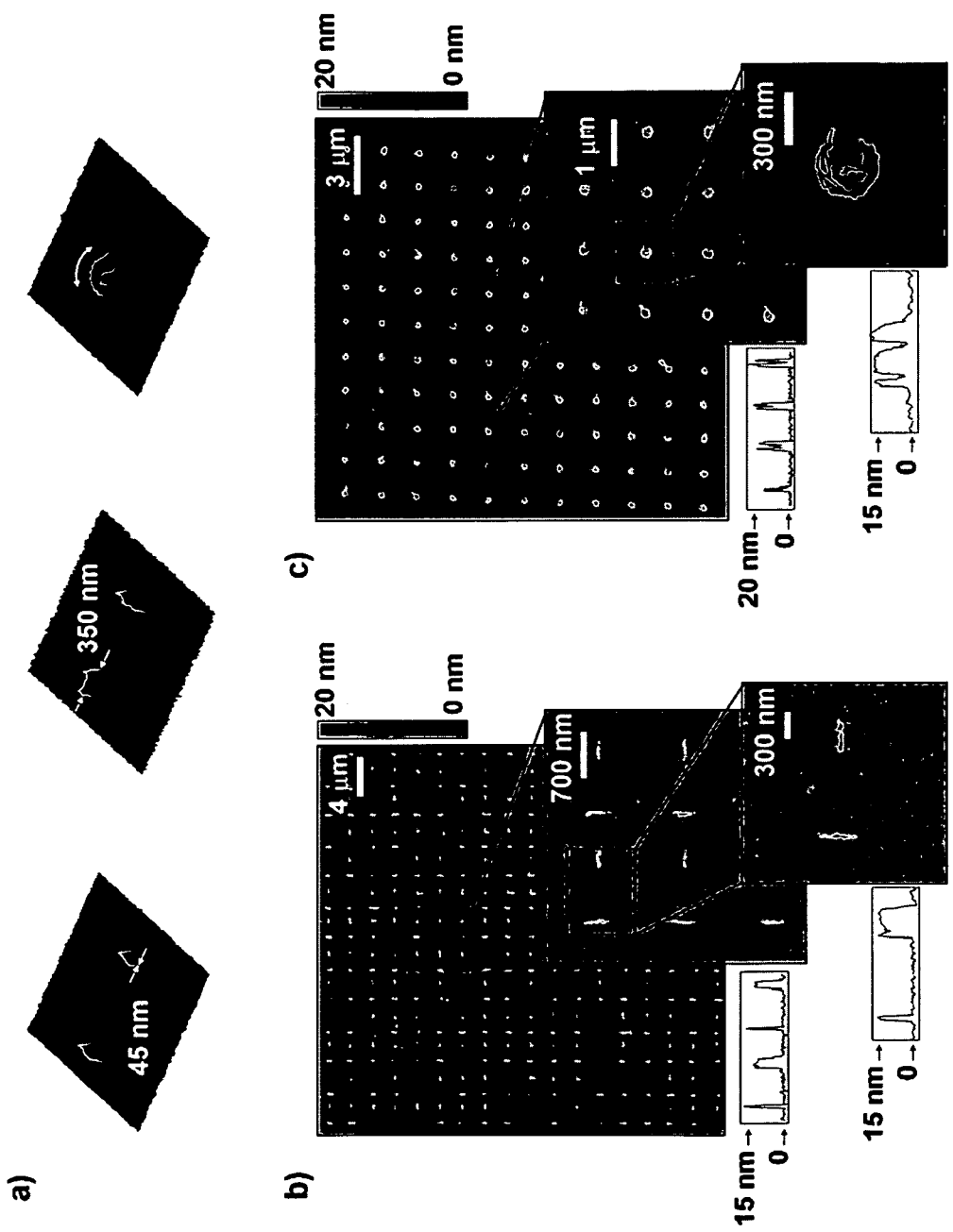
FIG. 3. AFM tapping mode (using a silicon cantilever, spring constant=~40 N/m) images and height profiles of TMV nanoarrays. (a) Three-dimensional topographical images of pairs of virus particles within larger arrays: (left) a parallel array, (middle) a perpendicular array, and (right) dot arrays. (b) Topography images and height profiles of a perpendicular array of single virus particles (40×40 microns). (c) Topography image and height profiles of a TMV nanoarray (20×20 microns) formed on an array of 350 nm MHA dot features pretreated with $Zn(NO_3)_2.6H_2O$. All images were taken at a scan rate of 0.5 Hz.

A series of DPN patterned linear nanostructures of MHA, which vary in dimensions (length and width: 600 nm×200 nm, 500 nm×180 nm, 400 nm×150 nm and 350 nm×110 nm) were systematically studied to determine the optimum feature size for single virus particle attachment. Under the conditions studied, MHA templates with feature dimensions of 350 nm×110 nm, spaced one micrometer apart, proved to be ideal for individual particle assembly. The tendency of each virus to occupy the largest number of coordination sites results in near-perfect alignment of all the virus particles along the long axis of each rectangular template (FIGS. 3a and 3b). The average height of each feature on the template was 16±1 nm. Furthermore, each virus particle on the lines was 45±2 nm wide and 320±40 nm long, parameters consistent with the presence of only one TMV particle on each MHA feature.[13]

Figure 5:
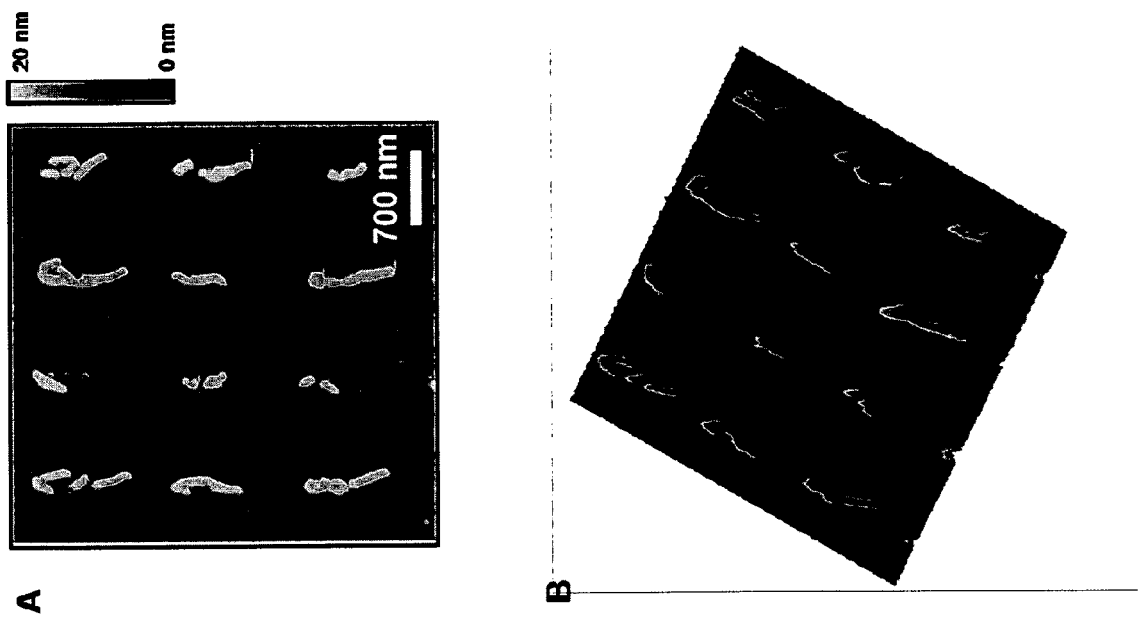
FIG. 5. AFM tapping mode (silicon cantilever, spring constant=about 40 N/m) 2D and 3D image of a TMV nanoarray formed on an MHA template consisting of 600 nm×200 nm rectangular features. More than one oriented virus is observed on each feature. The image was taken at a scan rate of 0.5 Hz.

The dimensions of the features within the array are critical for virus particle site isolation. For example, rectangular templates greater than 500 nm long or 200 nm wide yield multiple yet oriented viruses at each site, thus preventing the formation of a single virus particle array (see FIG. 5). Features significantly smaller (less than 300 nm×100 nm) do not result in uniform assembly of the virus particles with numerous sites remaining unoccupied.

The chemical templates also can be used to control the assembly of the flexible virus into unnatural conformations such as circles and other curved architectures. For example, 350 nm diameter dot templates can capture multiple virus particles, many of which adhere to the rim of the dot and adopt a curved architecture (FIG. 3c). Curved TMV structures have been made before but through mechanical manipulation of the virus.[14] This approach to virus bending is in contrast with the templated approach described in these studies.

To demonstrate that the virus orientation is not a result of external variables such as washing, drying via flowing $N_2$ or capillary effects, independent organization of each virus particle was tested by immobilization along two different directions within one array. Indeed, when an MHA template consisting of 350 nm×110 nm features perpendicular to one another was used, an array of site-isolated single TMV viruses perpendicular to each other was obtained (FIG. 3b).

Figure 4:
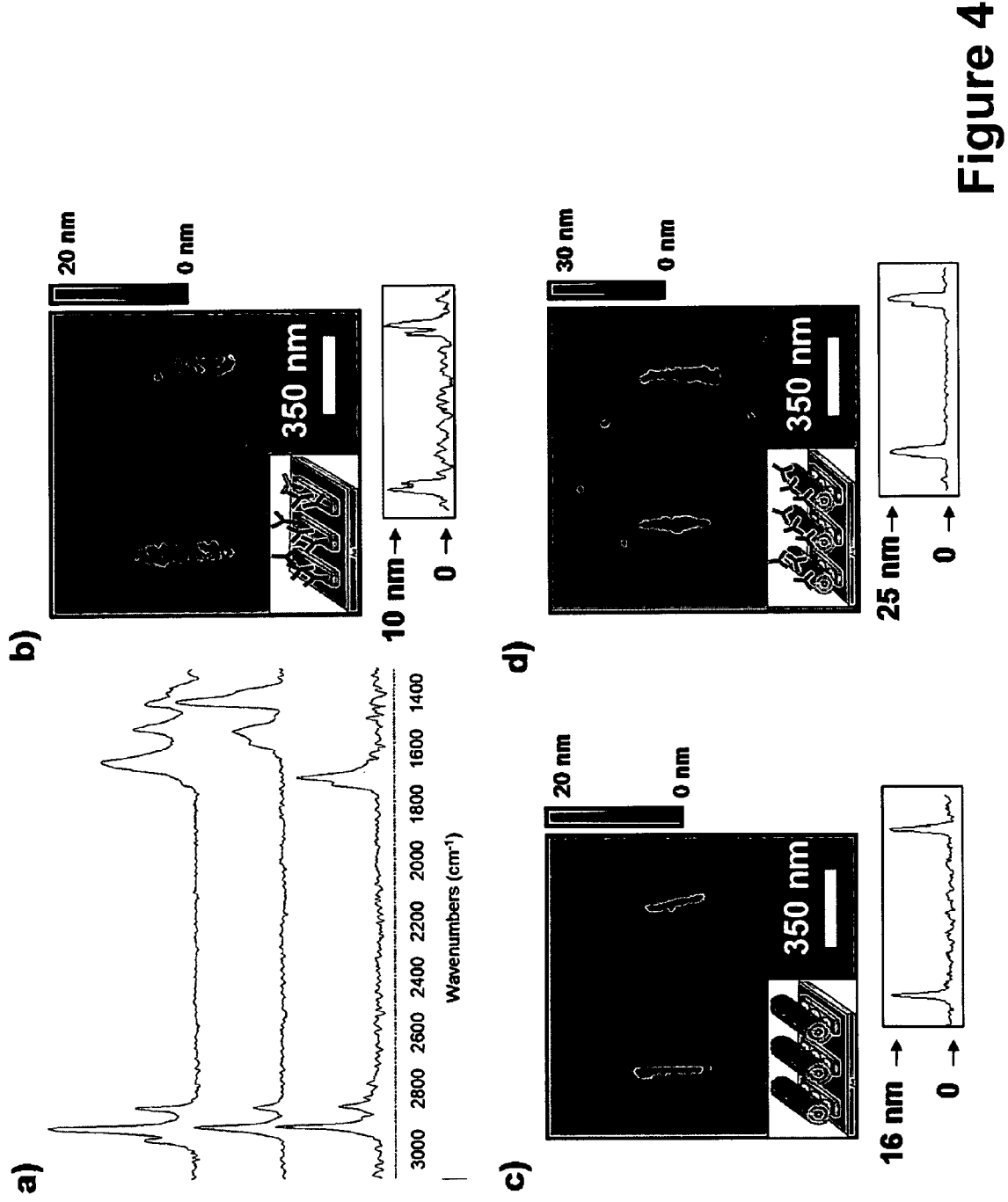
FIG. 4. (a) PM-IRRAS spectra of a monolayer of MHA on Au (bottom spectrum), after treatment with $Zn(NO_3)_2.6H_2O$ (middle spectrum), and then incubation with TMV (top spectrum). (b) Topography image and height profile of an MHA array treated with the antiserum against TMV. The antibodies are electrostatically attached to the MHA features. Topography images and height profiles of a pair of parallel single virus particles before (c) and after (d) treatment with a PBS solution containing the antiserum against TMV. All AFM images were taken at a 0.5 Hz scan rate in tapping mode.
Figure 6:
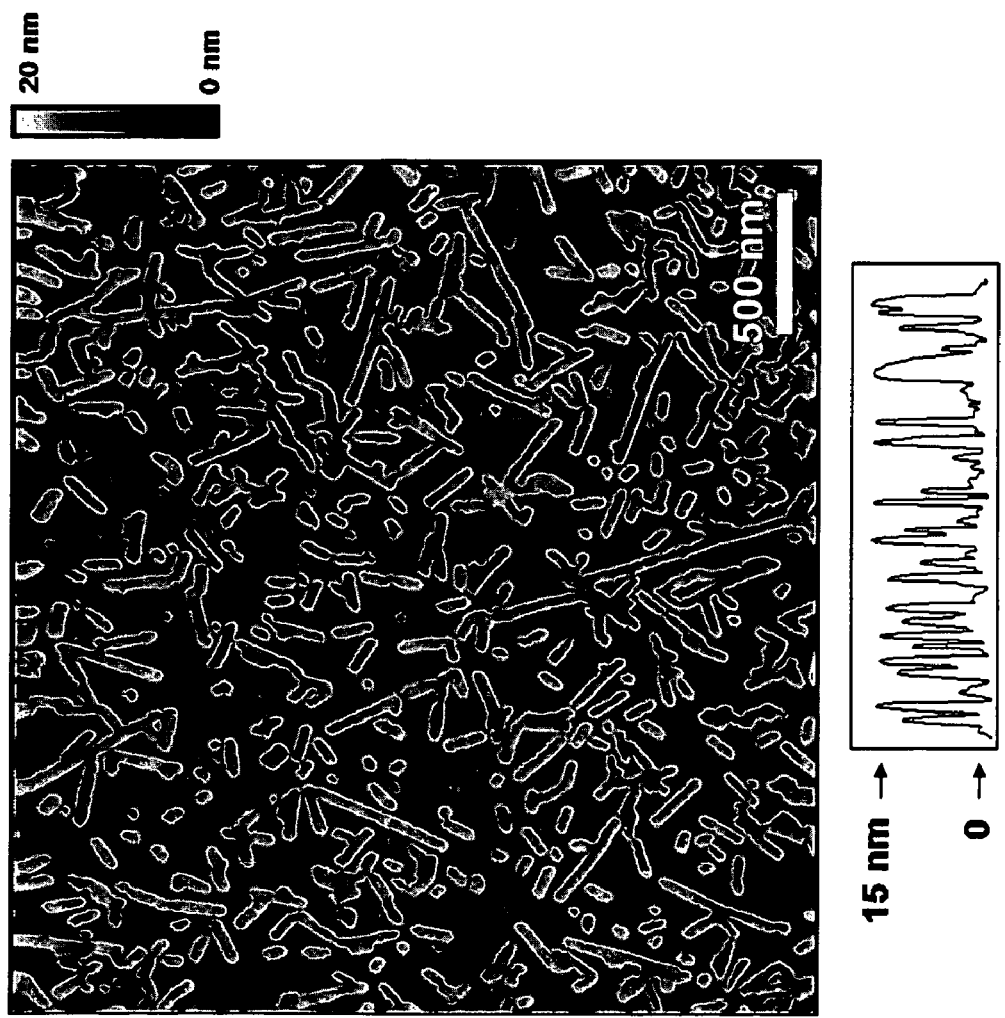
FIG. 6. AFM tapping mode (silicon cantilever, spring constant=about 40 N/m) image and height profile of a bulk gold thin film sample (7.5 cm×2.5 cm) containing a monolayer of TMV on a $Zn^{2+}$-MHA modified surface. This image was taken at a scan rate of 0.5 Hz.

Polarization modulation-infrared reflection-adsorption spectroscopy (PM-IRRAS) was used to characterize bulk gold thin film substrates modified with TMV using the same metal ion or coordination chemistry approach used to generate the TMV arrays (FIG. 4a and FIG. 6). The MHA monolayer exhibits two main bands in the high-frequency-$CH_2$-stretching region at 2856 and 2930 $cm^{-1}$ and two in the C=O stretching region at 1741 and 1718 $cm^{-1}$, which are attributed to the presence of free and hydrogen-bonded carboxylic groups,[15] respectively. After the substrate was immersed in an ethanolic $Zn(NO_3)2.6H_2O$ solution (5 mM) for 1 h, the coordination of MHA carboxylic groups to $Zn^{2+}$ metal ions was confirmed by ACO band shifts to lower energy (1602/1556 and 1453 cm-1). The C=O stretching region changes again after exposing the MHA-Zn surface to the TMV solution. Three main bands are detected in this spectral region that can be identified as the amide I band centered at 1661 $cm^{-1}$, which is characteristic of proteins on TMV,[16] the amide II and asymmetric COO— bands centered at 1546 $cm^{-1}$, and symmetric COO— band at 1458 $cm^{-1}$. Also the presence of $CH_3$ groups, attributed to proteins with methyl groups is confirmed by growth of a new band at 2967 $cm^{-1}$ after incubation with TMV.

In this working example, the coordination chemistry including the $Zn^{2+}$ coordination chemistry is believed important for the virus particle assembly process. Consistent with this conclusion, in control experiments, TMV will not assemble on MHA coated or patterned substrates (1 micron dot diameter), even after exposure of the template to a PBS solution of the virus for 48 hours.

Figure 7:
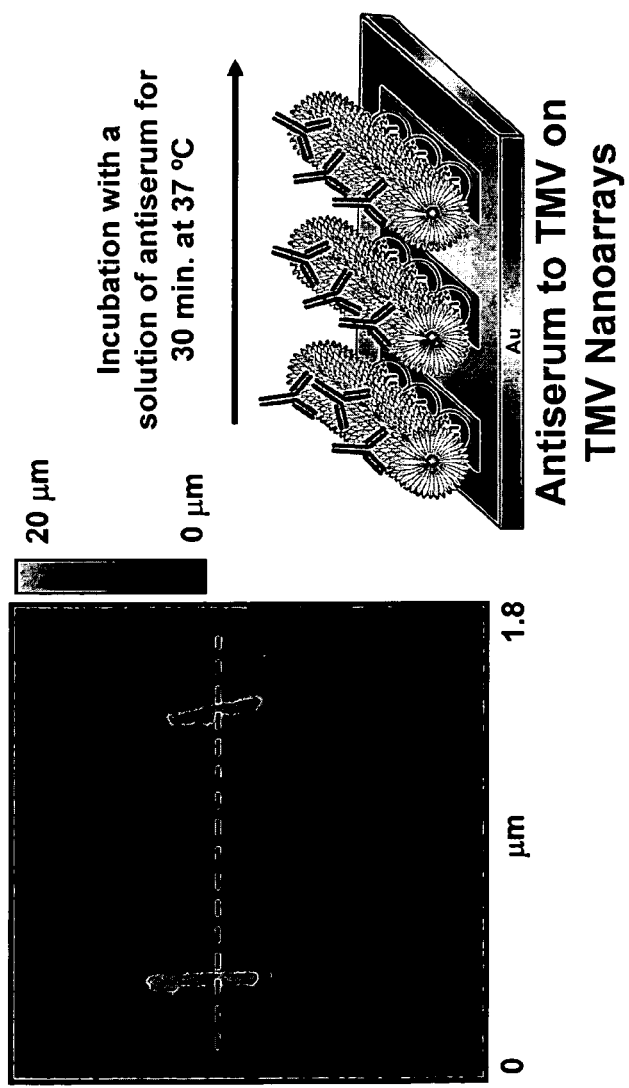
FIG. 7. Topography images from a tapping mode AFM (Vecco) of site-isolated TMV before and after (a, b respectively) incubation with a solution of antiserum for 30 min. at 37° C. The observed increase in height shows that antibodies have bound to the TMV and therefore that they are biologically active after immobilization.
Figure 7:

To provide further evidence for the chemical identity of the tubular virus structures imaged by AFM, we treated the single virus arrays with a PBS solution of an antiserum against TMV (200 microg/mL, pH 7) at 37° C. for 30 minutes, rinsed the substrates with 10 mM PBS solution and then dried them under a stream of $N_2$. A comparison of the AFM images of the substrate before and after incubation with antibody shows a height increase of approximately 9 nm (FIGS. 4c and 4d; see also FIG. 7). This increase is consistent with the height of the antibody (FIG. 4b) and therefore, the presence of TMV particles on the arrays. Antibody arrays were generated by first using DPN to pattern rectangular lines of MHA with feature dimensions of 350 nm×110 nm. The area around these features was passivated with PEG-SH for 30 minutes, followed by copious rinsing with ethanol to inhibit non-specific binding. Finally the antiserum to TMV was incubated with the MHA passivated substrate at 4° C. for 24 hours. For more details see reference[8].

Note that the expected height increase upon antibody binding was independently modeled and measured using direct adsorption of the antibody onto an MHA array (FIG. 4b). This approach has been used to study protein binding events in the context of other protein immobilization experiments.[8]

In some cases, not all of the binding sites will have a single virus, but substantially all binding sites will have a single virus. In some cases, at least 50%, or at least 60%, or at least 70%, or at least 80%, or at least 90% of the binding sites will have a single virus. Remaining sites can have more than one virus particle or in some cases no virus particle.

Experimental Section:

All DPN patterning was done with a ThermoMicroscopes CP AFM interfaced with commercialized lithographic software (DPNwrite™, Nanoink Inc., Chicago, Ill.) and conventional $Si_3N_4$ cantilevers (Thermo Microscopes sharpened Microcantilever A, force constant of 0.05 N/m). Tapping mode images were taken with a Nanoscope IIIa and Multi-Mode microscope from Digital Instruments. Unless noted otherwise, all DPN patterning experiments were conducted at 35% relative humidity and 24° C. with a tip-substrate contact force of 0.5 nN. DPN was used to pattern MHA on gold substrate (50 nm Au and 10 nm Cr on a silicon wafer, Silicon Sense, Inc.). PM-IRRAS spectra of 2048 scans at 4 cm−1 resolution were obtained with a Thermo Nicolet, Nexus 870 with Tabletop optics module (TOM). The PM-IRRAS differential reflectance (% ΔR/R) values were converted to absorbance units for comparison with conventional IRRAS data.

The following references are useful to practice the invention and are hereby incorporated by reference in their entirety:
[1] U. R. Miller, D. V. Nicolau, *Microarray Technology and Its Applications*, Springer, N.Y., 2005.
[2] K. Lindroos, S. Sigurdsson, K. Johansson, L. Ronnblom, A. C. Syvanen, *Nucleic Acid Res.* 2002, 30, e70-e78.
[3] M. Schena, D. Shalon, R. W. Davis, P. O. Brown, *Science* 1995, 270, 467-470.
[4] R. A. Heller, M. Schena, A. Chai, D. Shalon, T. Bedilion, J. Gilmore, D. E. Woolley, R. W. Davis, *Proc. Natl. Acad. Sci. USA* 1997, 94, 2150-2155.
[5] G. MacBeath, S. L. Schreiber, *Science* 2000, 289, 1760-1763.
[6] D. S. Ginger, H. Zhang, C. A. Mirkin, *Angew Chem. Int. Ed.* 2004, 43, 30-45.
[7] For an example of DNA nanoarrays see: L. M. Demers, D. S. Ginger, S.-J. Park, Z. Li, S.-W. Chung, C. A. Mirkin, *Science* 2002, 296, 1836-1838.
[8] For an example of protein nanoarrays see: K.-B. Lee, S.-J. Park, C. A. Mirkin, J. C. Smith, M. Mrksich, *Science* 2002, 295, 1702-1705.
[9] For an example of peptide nanoarrays see: J. Hyun, W. K. Lee, N. Nath, A. Chilkoti, S. Zauscher, *J. Am. Chem. Soc.* 2004, 126, 7330-7335.
[10] a) T. M. A. Wilson, R. N. Perham, *Virology* 1985, 140, 21-27; b) L. King, R. Leberman, *Biochem. Biophys. Acta* 1973, 322, 279-293.
[11] C. L. Cheung, J. A. Carnarero, B. W. Woods, T. Lin, J. E. Johnson, J. J. Yorero, *J. Am. Chem. Soc.* 2003, 125, 6848-6849.
[12] J. C. Smith, K.-B. Lee, Q. Wang, M. G. Finn, J. E. Johnson, M. Mrksich, C. A. Mirkin, *Nano Lett.* 2003, 3, 883-886.
[13] a) M. Knez, M. P. Sumser, A. M. Bittner, C. Wege, H. Jeske, D. M. P. Hoffmann, D. M. P. Kuhnke, K. Kern, *Langmuir* 2004, 20, 441-447; b) H. Maeda, *Langmuir* 1997, 13, 4150-4161; and references therein.
[14] M. Guthold, M. Falvo, W. G. Matthews, S. Paulson, J. Mullin, S. Lord, D. Erie, S. Washburn, R. Superfine, F. P. Brooks Jr., R. M. Taylor II, *J Mol. Graphics Mod.* 1999, 17, 187-197.
[15] B. L. Frey, R. M. Corn, *Anal. Chem.* 1996, 68, 3187-3193.
[16] R. D. B. Fraser, *Nature* 1952, 20, 491.
[18] G. Basu, M. Allen, D. Willits, M. Young, T. Douglas, *J. Biol. Inorg. Chem.* 2003, 8, 721-725.
[19] a) W. Shenton, T. Douglas, M. Young, G. Stubbs, S. Mann, *Adv. Mater.* 1999, 11, 253-256; b) E. Dujardin, C. Peet, G. Stubbs, J. M. Culver, S. Mann, *Nano Lett.* 2003, 3, 413-417; c) M. Knez, A. M. Bittner, F. Boes, C. Wege, H. Jeske, E. Mai, K. Kern, *Nano Lett.* 2003, 3, 1079-1082.

What is claimed is:

1. An array comprising:
A substrate surface comprising a pattern of binding sites for a virus,
wherein each binding site is surrounded by a substrate surface which does not bind virus,
wherein the shape and the size of the virus binding site provides that only one virus particle is disposed on each binding site, and
one virus particle disposed on each of the binding sites.

2. The array according to claim 1, wherein the substrate surface is substantially flat.

3. The array according to claim 1, wherein the sites which do not bind virus are passivated against virus binding.

4. The array according to claim 1, wherein the sites which do not bind virus are substantially free of virus.

5. The array according to claim 1, wherein the virus binding sites comprises ionic binding sites.

6. The array according to claim 1, wherein the virus binding sites comprise multivalent metal ions.

7. The array according to claim 1, wherein the average size of the virus binding sites provides a surface area of less than about 100,000 square nm for each site.

8. The array according to claim 1, wherein the average size of the virus binding sites provides a surface area of less than about 50,000 square nm for each site.

9. The array according to claim 1, wherein the average size of the virus binding sites provides a surface area of about 30,000 square nm to about 100,000 square nm for each site.

10. The array according to claim 1, wherein the shape of the virus binding sites is substantially a circle, a linear shape, a curvilinear shape, a square, or a rectangle.

11. The array according to claim 1, wherein the shape of the virus binding sites comprises a rectangle having a length of about 300 nm to about 600 nm, and a width of about 100 nm to about 200 nm.

12. The array according to claim 1, wherein the virus has an anisotropic shape.

13. The array according to claim 1, wherein the virus has a tubular shape.

14. The array according to claim 1, wherein the virus particle comprises an additional moiety bound to the virus.

15. The array according to claim 1, wherein the virus binding sites and sites which do not bind virus comprise a monolayer.

16. The array according to claim 1, wherein the shape and size of each of the virus binding sites are substantially the same, and the sites which do not bind virus are passivated against virus binding so that they are substantially free of virus.

17. The array according to claim 16, wherein the average size of the virus binding sites provides a surface area of less than about 100,000 square nm for each site.

18. The array according to claim 16, wherein the average size of the virus binding sites provides a surface area of less than about 50,000 square nm for each site.

19. The array according to claim 1, wherein the shape of the virus binding sites is substantially a circle, a linear shape, a curvilinear shape, a square, or a rectangle, and the shape and size of each of the virus binding sites are substantially the same.

20. An array comprising:
a plurality of virus binding sites on a substantially flat substrate surface, wherein each binding site is surrounded by substrate surface passivated against virus binding,
wherein the virus binding sites have a shape and size so that only one virus particle binds to each site,
wherein the average size of the virus binding sites provides a surface area of about 30,000 square nm to about 100,000 square nm for each site, one virus bound to each site, wherein the virus in an unbound shape presents a cross-sectional surface area which is less than about 100,000 square nm.

21. The array according to claim 20, wherein the virus is a wild type virus.

22. The array according to claim 20, wherein the binding sites comprise metal ions.

* * * * *

UNITED STATES PATENT AND TRADEMARK OFFICE
CERTIFICATE OF CORRECTION

| | |
|---|---|
| PATENT NO. | : 7,569,340 B2 |
| APPLICATION NO. | : 11/506200 |
| DATED | : August 4, 2009 |
| INVENTOR(S) | : Chad A. Mirkin et al. |

It is certified that error appears in the above-identified patent and that said Letters Patent is hereby corrected as shown below:

In the Specification:

Column 1, line 19-20, in the paragraph under the heading "GOVERNMENT RIGHTS"; please replace "ARO-MURI 28065-3-A1//W91NF-04-1-071" with
-- ARO-MURI 28065-3-A1//W911NF-04-1-071 --.

Signed and Sealed this
Twenty-second Day of March, 2011

David J. Kappos
*Director of the United States Patent and Trademark Office*